United States Patent [19]

Baumgarten et al.

[11] 4,391,887

[45] Jul. 5, 1983

[54] PREPARATIONS OF MICRO-ORGANISMS

[75] Inventors: Jörg Baumgarten; Werner Frommer; Delf Schmidt; Friedrich Schmidt, all of Wuppertal, Fed. Rep. of Germany; Douglas M. Munnecke, Norman, Okla.

[73] Assignee: Bayer Aktiengesellschaft, Leverkusen, Fed. Rep. of Germany

[21] Appl. No.: 292,362

[22] Filed: Aug. 13, 1981

Related U.S. Application Data

[63] Continuation of Ser. No. 945,287, Sep. 25, 1978, abandoned.

[30] Foreign Application Priority Data

Dec. 15, 1977 [DE] Fed. Rep. of Germany ....... 2756032

[51] Int. Cl.$^3$ .................. C12P 39/00; C12N 1/36; C12N 1/04; C12N 1/20
[52] U.S. Cl. .................. 435/42; 435/245; 435/260; 435/261; 435/262; 435/874; 435/253; 210/610; 210/611; 210/906
[58] Field of Search .......... 435/43, 245, 244, 253, 435/255, 260, 262, 821; 210/610, 611, 906

[56] References Cited

U.S. PATENT DOCUMENTS 3,660,278  5/1972  Mimura et al. .................. 260/611
4,094,097  6/1978  Alexander et al. ............. 435/245 X

FOREIGN PATENT DOCUMENTS 52-57389  5/1977  Japan .................................. 435/245

OTHER PUBLICATIONS

Munnecke et al., Applied Microbiology, vol. 28, No. 2, pp. 212–217, Aug. 1974.
Munneck, Applied and Environmental Microbiology, vol. 32, No. 1, pp. 7–13, Jul. 1976.

Primary Examiner—Lionel M. Shapiro
Attorney, Agent, or Firm—Sprung, Horn, Kramer & Woods

[57] ABSTRACT

A process for the production of a storage-stable preparation of micro-organisms, starting from a mixed culture of micro-organisms, which is capable to degrade products of industrial organic syntheses, which comprises that the culture conditions of an active mixed culture enriched in the customary manner are optimized, with the addition of the product to be degraded, in the customary manner according to the rate of degradation of the product and this mixed culture is converted in at least two passes into a stabilized activated mixed culture under the optimum conditions thus determined, and the culture thereby obtained is rendered storage-stable, its activity being maintained.

13 Claims, No Drawings

PREPARATIONS OF MICRO-ORGANISMS

This is a continuation of application Ser. No. 945,287, filed Sept. 25, 1978 now abandoned.

The present invention relates to certain new preparations of micro-organisms, to a process for producing them and to their use for the degradation of products of industrial organic syntheses.

It is known to degrade effluents containing organic synthesis products as impurities in purification plants by the activated sludge process. In this process, the effluents are aerated in large basins, and in the course of time the effluents become enriched with certain microorganisms which carry out the desired degradation. However, stable preparations with which certain products can be degraded cannot be isolated from the microorganism compositions thereby obtained since the degradation activity of these micro-organism compositions is inadequate for this degradation and in addition is at least partly lost during working up.

It is also known that baker's yeast degrades starch and sugar during the preparation of the dough. However, it is difficult to render these baker's yeasts stable as permanent powders, for example as dried yeast powders, whilst maintaining their full activity. Moreover, dried baker's yeast can be kept without substantial loss in activity only in vacuo or under an inert gas atmosphere (see G. Reed et al., Yeast Technology, 1973, West Port, Avi Publication Comp.).

It has furthermore been disclosed that micro-organisms living in the soil degrade insecticidal active compounds, in particular phosphoric acid esters and carbamates (see the review article by J. Laveglia et al., Annual Review of Entomology 1977, 22, page 483 et seq., and the literature references indicated therein).

It has also been disclosed that mixed cultures of micro-organisms are suitable for the degradation of insecticidal active compounds, such as parathion. However, such cultures are relatively inactive and can be handled only with difficulty. Preparations which have hitherto been obtained from such cultures were themselves unstable at $-18°$ C. and could not be produced in a solid form (see Munnecke et al., Applied Environ. Microbiology, 1976, 32, page 7–13).

1. It has now been found that new storage-stable preparations of micro-organisms are obtained, starting from stabilised activated mixed cultures of micro-organisms which are used for the degradation of products of industrial organic syntheses, by a process in which the culture conditions of an active mixed culture enriched in the customary manner are optimised, with the addition of the product to be degraded, in the customary manner according to the rate of degradation of the product and this mixed culture is converted in at least two passes into a stabilised activated mixed culture under the optimum conditions thus determined, and the culture thereby obtained is rendered storage-stable by preserving it, its activity being maintained.

2. It has furthermore been found that the new storage-stable preparations of micro-organisms can be produced on an industrial scale, starting from stabilised activated mixed cultures of micro-organisms, by a process in which stabilised activated mixed cultures which have been produced as described under 1. are used directly or, if they have been rendered storage-stable without loss in their vitality, in the form of their preserves, as the inoculum, and the industrial production is carried out under the conditions given under 1. and the resulting culture is carefully dried, its activity being maintained.

3. It has also been found that new storage-stable preparations of micro-organisms are obtained, starting from activated pure cultures of amicro-organisms which are used for the degradation of products of industrial organic syntheses, by a process in which individual strains of the mixed culture obtained under 1. are grown on complex media used in customary manner, these strains are selected according to their activity and the active strains are cultivated under sterile conditions in the customary manner, during which the product to be degraded can be present in the substrate, and the resulting culture is carefully dried, its activity being maintained.

4. The new storage-stable preparations of micro-organisms, starting from stabilised activated mixed cultures of micro-organisms, which are used for the degradation of products of industrial organic syntheses and are obtained according to process 1 or 2 have also been found.

5. The new storage-stable preparations of micro-organisms, starting from activated pure culutres of micro-organisms, which are used for the degradation of products of industrial organic syntheses and are obtained according to process 3 have furthermore been found.

6. New strains of micro-organisms have additionally been found.

It was surprising that it was possible, by the process according to the invention, to obtain storage-stable preparations of micro-organisms. It was hitherto possible to stabilise such preparations only by bonding solubilised enzymes to carriers, for example glass (compare Munnecke, Applied Environ. Microbiology, 1977, 33, page 503–507). However, high losses in activity occur in this process. Only by the process according to the invention was it possible to produce preparations of micro-organisms which are storage-stable even under industrial conditions, which retain their full activity over a long period and which can be used simply, rapidly and economically. It was surprising that these preparations retain their activity without it being necessary to isolate the enzymes responsible for the activity.

It was also known that mixed cultures of microorganisms are difficult to handle on an industrial scale. It was therefore surprising that a stabilised activated mixed culture can be obtained with can also be handled on an industrial scale.

The cell preparations obtainable by the process according to the invention are used for the degradation of products of industrial organic syntheses at places where these are undesired. They can be employed, for example, for the treatment of effluents which are obtained during the production of organic products, for cleaning transport containers and for disposing of, or rendering harmless, pollution caused by accidents. They are also suitable for the decontamination of skin and soil.

By products of industrial organic syntheses there are understood organic compounds which are produced industrially by chemical synthesis processes. (By these there are not to be understood organic compounds, on an industrial scale, originating from natural sources.) In the sense of the invention, products of industrial organic syntheses include, for example:

(1) plant protection agents, in particular insecticides, and furthermore herbicides and fungicides;

(2) pharmaceuticals;
(3) dyestuffs, in particular azo dyestuffs and anthraquinone dyestuffs;
(4) organic intermediate products, especially monomers which are used for polymerisation, such as nitriles, and auxiliaries for the production of rubber, such as sulphonic acids, and organic solvents, such as aromatics.

The insecticides include:
(A) carbamates;
(B) carboxylic acid esters, including the pyrethroids;
(C) phosphoric acid esters;
(D) cycloalkanes;
(E) halogenalkanes.

The carbamates (A) include those of the general formula

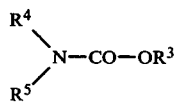

(I)

in which
R³ represents aryl, a heterocyclic radical or an oxime radical,
R⁴ represents hydrogen or alkyl with 1 to 4 carbon atoms and
R⁵ represents alkyl, alkylcarbonyl with 1 to 6 carbon atoms in the alkyl radical, which can also be optionally substituted by hydroxyl or methylthio, or the radical —S—Z,
wherein
Z represents an aliphatic radical with 1 to 4 carbon atoms which is optionally substituted by halogen (especially CCl₃ and CF₃) or represents an aryl radical, in particular phenyl, which is optionally substituted, preferably by nitrile, halogen (especially chlorine), methyl, trihalogenomethyl, trifluoromethylmercapto or nitro, or represents methyoxycarbonyl or represents the radical

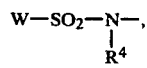

wherein
W represents alkyl, halogenoalkyl, alkylamino, dialkylamino or an aryl radical which is optionally substituted, preferably by halogen, trihalogenomethyl, nitrile, methyl or nitro. Particularly preferred carbamates of the formula (I) are those in which
R³ represents phenyl or naphthyl, either of which is optionally substituted by alkyl, alkenyl, alkoxy, alkylmercapto or alkylthioalkylene with in each case 1 to 5 carbon atoms, dialkylamino or dialkenylamino with up to 3 carbon atoms per alkyl part or alkenyl part, halogen (especially chlorine), dioxolanyl or the radical -N=CH-N(C₁₋₄-alkyl)₂, or
R³ represents 2,3-dihydrobenzofuranyl, benzodioxolyl, benzothienyl, pyrimidinyl or pyrazolyl, each of which is optionally substituted by C₁₋₄-alkyl (especially methyl), or dialkylamino with 1 to 4 carbon atoms per alkyl part, or
R³ represents an oxime radical of the general formula

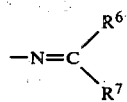

(Ia)

in which
R⁶ and R⁷ are identical or different and represent alkyl, cycloalkyl, alkenyl, alkynyl, alkoxy, alkylmercapto, alkoxycarbonyl, carbonylamide or alkylmercaptoalkyl with in each case up to 5 carbon atoms, nitrile, aryl (especially phenyl), or an optionally substituted heterocyclic radical, or represent alkyl which is substituted by a heterocyclic radical, or together represent a dioxolanyl or dithiolanyl radical optionally substituted by C₁₋₄-alkyl.

The following carbamates may be mentioned in particular: 2-methylphenyl, 2-ethylphenyl, 2-n-propylphenyl, 2-methoxyphenyl, 2-ethoxyphenyl, 2-iso-propoxyphenyl, 4-methyl-phenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-[1,3-dioxolan-2-yl-phenyl] and 2,2-dimethyl-1,3-benzodioxol-4-yl N-methyl-carbamate and the corresponding N-methyl-N-acetyl-, N-methyl-N-trifluoromethylthio-, N-methyl-N-dichloromonofluoromethylthio- and N-methyl-N-dimethylaminothiocarbamates.

The carboxylic acid esters (B) include those of the general formula

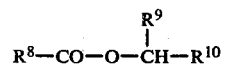

(II)

in which
R⁸ represents alkyl, aralkyl, aryl or cycloalkyl which can be optionally substituted,
R⁹ represents hydrogen, alkyl, halogenoalkyl, alkenyl, alkynyl or nitrile and
R¹⁰ represents aryl or a heterocyclic radical or, together with R⁹, forms an optionally substituted cyclopentenone ring. Particularly preferred carboxylic acid esters of the formula (II) are those in which
R⁸ represents alkyl with 1 to 6 carbon atoms which is optionally substituted by optionally substituted pjenyl, or cyclopropyl which is optionally substituted by alkyl, alkenyl, halogenoalkyl or halogenoalkenyl with in each case up to 6 carbon atoms, or represents phenyl which is optionally substituted, and/or
R⁹ represents hydrogen, alkyl with 1 to 6 carbon atoms, halogenoalkyl with 1 to 4 carbon atoms and up to 3 halogen atoms, nitrile or ethynyl, and/or
R¹⁰ represents phenyl which is optionally substituted by C₁₋₄-alkyl, halogen (especially fluorine or chlorine), optionally substituted phenoxy or optionally substituted benzyl, or represents furanyl, tetrahydrophthalimido or benzodioxolyl each of which is optionally substituted by halogen (especially chlorine), alkyl or alkenyl with up to 4 carbon atoms or benzyl, or alternatively represents cyclopentenone which is optionally substituted by C₁₋₄-alkyl, furfuryl or C₁₋₅-alkenyl.

The following carboxylic acid esters may be mentioned in particular: acetic acid 1-(3,4-dichlorophenyl)-

2,2,2-trichloroethyl ester, 2,3,4,5-tetrahydrophthalimido-methyl chrysanthemate and (5-benzyl-3-furyl)-methyl 2,2-dimethyl-3-(2-methylpropenyl)-cyclopropane-carboxylate.

The phosphoric acid esters (C) include those of the general formula

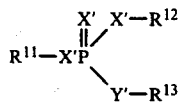

in which
the symbols X' independently of one another represent O or S,
Y' represents O, S or -NH-, or represents a direct bond between the central P atom and the radical $R^{13}$,
$R^{11}$ and $R^{12}$ are identical or different and represent alkyl or aryl and
$R^{13}$ represents alkyl, aryl, hetero-aryl, aralkyl, alkenyl, dioxanyl or an oxime radical, or represents a radical identical to the radical to which it is bonded. Particularly preferred phosphoric acid esters of the formula (III) are those in which
$R^{11}$ and $R^{12}$ are identical or different and represent $C_{1-4}$-alkyl or phenyl and
$R^{13}$ represents alkyl with 1 to 4 carbon atoms which is optionally substituted by halogen, hydroxyl, nitrile, optionally substituted phenyl, carbonylamide, sulphonylalkyl, sulphoxyalkyl, carbonylalkyl, alkoxy, alkylmercapto or alkoxycarbonyl, or represents alkenyl with up to 4 carbon atoms which is optionally substituted by halogen, optionally halogen-substituted phenyl or alkoxycarbonyl, or represents the oxime radical of the general formula

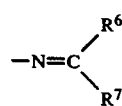

wherein
$R^6$ and $R^7$ have the meanings stated above (especially cyano or phenyl), or
$R^{13}$ represents dioxanyl which is substituted by a radical identical to the radical to which $R^{13}$ is bonded, or
$R^{13}$ represents a radical identical to the radical to which it is bonded, or
$R^{13}$ represents phenyl which is optionally substituted by methyl, nitro, nitrile, halogen or methylthio, or
$R^{13}$ represents a heteroaromatic radical, such as pyridine, quinoline, quinoxaline, pyrimidine, diazinone and benzo-1,2,4-triazine, which is optionally substituted by $C_{1-4}$-alkyl or halogen.

The following phosphoric acid esters may be mentioned in particular: O,O-dimethyl- and O,O-diethyl-O-(2,2-dichloro- and 2,2-dibromo-vinyl)-phosphoric acid esters, O,O-diethyl-O-(4-nitro-phenyl)-thionophosphoric acid ester (=parathion), O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthio-phenyl)-thionophosphoric acid ester, O,O-dimethyl-S-[4-oxo-1,2,3-benzotriazin-3-yl-methyl]-thionothiolphosphoric acid ester, O-methyl-O-[2-iso-propyl-6-methoxy-pyrimidin-4-yl]-thionomethanephosphonic acid ester, O,O-diethyl-O-[2-iso-propyl-6-methyl-pyrimidin-4-yl]-thionophosphoric acid ester, O,O-diethyl-O-[3-chloro-4-methyl-coumarin-7-yl]-thionophosphoric acid ester, O,O-dimethyl-2,2,2-trichloro-1-hydroxy-ethane-phosphonic acid ester and O,O-dimethyl-S-(methylcarbamoylmethyl)-thionophosphoric acid ester.

The cycloalkanes (D) include those of the general formula

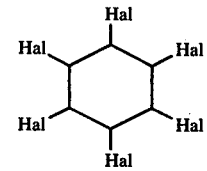

in which
Hal denotes halogen.
1,2,3,4,5,6-Hexachlorohexane may be mentioned in particular.

The halogenoalkanes (E) include those of the general formula

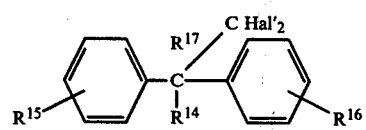

in which
Hal' represents chlorine or bromine,
$R^{14}$ represents hydrogen or hydroxyl,
$R^{15}$ and $R^{16}$ are identical or different and represent halogen, alkyl or alkoxy and
$R^{17}$ represents hydrogen or halogen.

Particularly preferred halogenoalkanes of the formula (V) are those in which
$R^{14}$ denotes hydrogen or hydroxyl,
$R^{15}$ and $R^{16}$ represent identical halogen, or alkyl or alkoxy each with 1 to 4 carbon atoms and
$R^{17}$ denotes halogen.

The following halogenoalkanes may be mentioned in particular: 1,1,1-trichloro-2,2-bis-(4-chloro- and 4-methoxyphenyl)-ethane, 1,1,1-trichloro-2-hydroxy-2,2-bis-(4-chlorophenyl)-ethane and 1,1-dichloro-2,2-bis-(4-ethylphenyl)-ethane.

The dyestuffs to be degraded include: anthraquinone dyestuffs, azo dyestuffs, methine dyestuffs, phenoxazine dyestuffs and triphenylmethane dyestuffs.

The organic intermediate products to be degraded include: simple nitriles, such as acetonitrile and isobutyronitrile; nitriles with an amino group in the α-position, for example α-aminopropionitrile, α-amino-γ-methylthiobutyronitrile, α-aminobutyronitrile and amino-acetonitrile; nitriles with a hydroxyl group in the α-position, for example lactonitrile, hydroxyacetonitrile and α-hydroxy-γ-methylthiobutyronitrile; nitriles with an amino group in the β-position, for example amino-3-propionitrile; dinitriles, such as malononitrile, succinonitrile and adiponitrile; α-unsaturated nitriles, such as acrylonitrile and methacrylonitrile; α-arylnitriles, such as homoveratronitrile and benzonitrile; and heterocyclic nitriles, such as nicotinonitrile and isonicotinonitrile.

The organic intermediate products furthermore include: acet(yl)gamma acid, acet(yl)-H-acid, acet(yl)-I-acid, acet(yl)-K-acid, alenic acid, alpha-naphthoic acid, alpha-naphthylic acid, alphamine, alpha-hydroxynaphthoic acid, alpha-acid, amido-E-acid, amino-C-acid, amino-Chicago acid (148), aminocroceic acid, amino-epsilon-acid, amino-F-acid, amino-G-acid, amino-Geigy acid, amino-I-acid, 2,3-aminonaphthol, aminonaphthol (acid) R, amino-R-acid, amino-R,R-acid, amino-Schaeffer's ether (acid), amino-Schaeffer's acid, Andresen's acid, Armstrong's acid, ethyl-beta-naphthamine, ethyl-chromotropic acid, azurine base, azuric acid, B-acid, Badische acid, Bayer acid, benzenesulphogamma-acid ester, benzenesulpho-R-R-acid, benzoyl-H-acid, benzoyl-I-acid, benzoyl-K-acid, beta-naphthoic acid, beta-acid, Boeniger acid, Broenner acid, C-acid, Casella acid, Chicago acid SS, chromotropic acid (4G and C), 1,6- and 1,7-Cleve's acid, Columbia acid, croceic acid, D-acid, Dahl's acid, delta-acid, Diaminogen acids, dimethyl-gamma-acid, Dinah acid, dinol, dihydroxy-Chicago acid, dihydroxy-F-acid, dihydroxy-G-acid, dihydroxy-I-acid, Dressel's acid, E-acid, eikonogen, epsilon-acid, F-acid, flavianic acid, Freund acid 136, Freund acid 137, G-acid, gamma-acid, Geigy acid, H-acid, H-acid esters, H-acid sulphamide, I-acid, I-acid urea, I-diacid, imidazole-I-acid, iso-Columbia acid, iso-I-acid, isoneu salt, K-acid, Koch's acid, L-acid, Laurent acid, M-acid, melanic acid, metazolic acid, methylamino-F-acid, methyl-beta-naphthamine, methylparazole-I-acid, Meyer-Landshoff acid, musizine, naphthalenedioic acid F, naphthalene salt, naphthaminedioic acid 147, naphthaminedioic acid 157, naphthamine acid 13, naphthaminetrioic acid 1,247 and 1,248, naphthaminetrioic acid 2,157, naphthaminetrioic acid K, o-naphthionic acid, naphthionic acid, naphtholdisulphonic acid C, naphtholdisulphonic acid F, naphtholdisulphonic acid S, Naphthol Yellow, naphthol-I-acid, naphthol acid 13, naphthol acid FF, naphthol acid P, naphthol acid S, naphtholsulphonic acid 21, naphtholtri(sulphonic) acid RR, naphtholtri(sulphonic) acid T, naphthylaminedisulphonic acid I, naphthylaminedisulphonic acid S, naphthylenic acid 125, Nekal BX, new salt, Nevile and Winther's acid, nitrotinic acid, nitrodiazoamidol acid, nitrodiazo-Boeniger acid, nitroso-R-acid, o-naphthionic acid, 5-hydroxy-C-acid, hydroxy-Chicago acid, hydroxy-Koch's acid, hydroxy-L-acid, hydroxynaphthoic acid 21, 8-hydroxynaphthylic acid, hydroxy-R-acid, hydroxy-Tobias acid, paradurol, parazole-I-acid, patrol-I-acid, peri-acid, phenyl-gamma-acid, purpuric acid, purpurol, purpurol acid, R-acid, 2R-acid, R.G.-acid, rhoduline acid, RM acid, red acid I, RR acid, SS-acid, acid IV, acid of Rudoll and Guerke, Schaeffer's acid, Schaeffer's-K-acid, Scheide's salt, Schoellkopf's acid, sulphamidic acid, sulphoethyl-gamma-acid, sulpho-gamma-acid, sulpho-I-acid, sulphonaphthylic acid 6, sulphonaphthylic acid 8, black acid, T-acid, tetra-acid, Tobias acid, trihydroxy-R-acid, tri-salt, violet acid (N) and W-acid, and furthermore phenol, nitrophenol, chlorophenols, chloronitrophenols, benzene, chlorobenzenes and anilines.

Either new or known mixed cultures of micro-organisms which have the property of degrading certain organic synthesis products are used as starting materials in the process according to the invention for producing the new preparations.

New mixed cultures are obtained by a process in which samples are taken from soils, activated sludges in purification plants, surface waters or surfaces which, under non-sterile conditions, continually come into contact with the products to be degraded, (for example walls and floors of production plants) and are cultivated under the customary conditions with the products to be degraded. The cultivation is repeated in several passes until an active mixed culture is obtained which can split the product to be degraded. However, it is also possible to carry out the cultivation continuously, the product to be degraded being used in the substrate.

Such mixed cultures can consist of protozoa, algae, blue-green algae, yeasts, fungi, bacteria and mixtures of any of these. Mixed cultures of fungi and/or bacteria are particularly preferred.

The fungi include: Myxomycetes, Acrasiales, Phycomycetes, Ascomycetes and yeasts, Basidiomycetes as well as Deuteromycetes.

The bacteria include: phototropic bacteria, such as Rhodospirillaceae, Chromatiaceae and Chlorobiaceae; creeping bacteria, such as Myxococcaceae, Archangiaceae, Cystobacteriaceae, Polyangraceae, Cystophagaceae, Beggiatoaceae, Simonsiellaceae, Leucotrichaceae; sheated bacteria, such as Sphaerotilus, Leptothrix and Streptothrix; budding and stalked bacteria, such as Hyphomicrobium, Hyphomonas, Pedomicrobium, Caulobacter, Gallionella and Nevskia; spiral bacteria, such as Sperillaceae; furthermore: Achromatiaceae, Pseudomonadaceae, Azotobacteraceae, Rhizobiaceae, Methylomonadaceae, Halobacteriaceae, Alcaligenes, Acetobacter, Enterobacteriaceae, Vibrionaceae, Zymomonas, Chromobacterium, Flavobacterium, Haemophilus, Actinobacillus, Streptobacillus, Desulphovibrio, Selenomonas, Neisseriaceae, Acinetobacter, Nitrobacteraceae, Thiobacillus, Thiobacterium, Siderocapsaecaea, Methanobacteriaceae, Micrococcaceae, Streptococcaceae, Peptococcaceae, Bacillaceae, Lactobacillaceae, Corynebacterium, Arthrobacter, Cellulomonas, Kurthia, Propionibacteriaceae, Actinomycetales, Mycobacteriaceae, Actinoplanaceae and Nocardiaceae.

The optimum culture conditions for the degradation to be carried out are now determined for the active mixed cultures thus obtained.

For this, it is necessary to match the following parameters:
1. Temperature.
2. pH value.
3. Partial pressure of oxygen.
4. Mineral salt content, for regulating the supply of nitrogen, phosphorus, sulphur, calcium, iron, heavy metals and the like.
5. Metering of the product to be degraded, both in terms of quantity and continuously or discontinuously.
6. Culture period.
7. Stirring speed.
8. Formulation auxiliaries for the product to be degraded, especially in the case of sparingly soluble products.

In order to establish the optimum culture conditions, these parameters are now varied, both individually and in combinations, and the activity is continuously monitored during degradation of the product to be degraded. The culture conditions thereby determined with respect to the individual parameters are in the following ranges:
1. Temperature 10°–70° C.
2. pH value 1–10
3. Oxygen concentration 0–48 mg/l 4. Phosphate content $PO_4^{(3-)}$ 0.00–10 g/l, nitrogen-containing salts (as $NH_4Cl$) 0–50 g/l, magnesium (as $MgSO_4$) 0.01–2 g/l, iron (as a salt) 0.01–0.1 g/l, calcium (as $CaCl_2$) 0.00–0.1 g/l and trace elements, such as for example, Cu, Co, Mn, Zn and Ba, inter alia.
5. The product to be degraded is added either in a growth-limiting concentration or in excess. In the case of growth-limiting concentration, it can also be added continuously at a flow rate adapted to correspond to the growth.
6. The culture period is between 5 hours and 14 days,
7. Stirring speed on a laboratory scale between 0 and 1,500 revolutions per minute.
8. Emulsifying agents and dispersing agents used are, for example, non-ionic and anionic emulsifiers, such as polyoxyethylene fatty acid esters, polyoxyethylene fatty alcohol ethers, for example, alkylaryl polyglycol ethers, alkylsulphonates, alkyl-sulphates, arylsulphonates and albumin hydrolysis products, for example lignin-sulphite waste liquors and methylcellulose.

By a combination of these measures, the mixed culture is stabilised to the extent that it is possible to work under non-sterile conditions without a reduction in activity occurring.

The active mixed cultures are then converted in at least two, in general from 2 to 50, passes into a stabilised activated mixed culture under the optimum culture conditions determined.

In this procedure, as many passes are carried out, on a relatively small scale (low batch volume), as are necessary to obtain a mixed culture in which in further passes no further increase in the properties causing the degradation of organic synthesis products takes place. The mixed culture thus obtained is called a stabilised activated mixed culture.

The stabilised activated mixed cultures are rendered storage-stable. This can be effected by freezing the culture or drying it carefully, for example by lyophilisation, removal of water with organic solvents or spray-drying, or by rendering the culture stable by adding preserving chemicals, such as citric acid, benzoic acid, formic acid, malicyclic acid, sugar or sodium chloride.

A preferred method of rendering the culture storage-stable, above all on a large industrial scale, is to separate off the micro-organism composition from the culture broth and to dry it by lyophilisation or by removing the water with organic solvents.

If a method of rendering the stabilised activated mixed culture, obtained as described above, storage-stable is chosen with which the vitality is not lost, the preparation can be kept and used as an inoculum for further batches, for example large-scale industrial batches. Such ways of rendering the culture storage-stable without loss in the vitality are, for example, freezing the culture broth and string it at temperatures below 0° C., with or without the addition of protective substances, such as, for example, glycerol or dimethylsulphoxide, lyophilisation or preserving in liquid nitrogen. The resulting preserves of stabilised activated mixed cultures can then be used at any time as an inoculum for large-scale industrial batches.

Such large-scale industrial batches are treated batch-wise in the customary manner under the optimum conditions indicated above, the stabilised activated mixed culture obtained as described above being employed as the inoculum directly or in the form of its preserves.

In the case of cultivation of the stabilised activated mixed cultures on a large industrial scale, it can be advantageous to employ the product to be degraded, depending on its propeties, either directly or in the form of a formulation which permits good uniform mixing of the product in the entire batch, or together with suitable emulsifying agents or dispersing agents.

Pure cultures can be obtained in the customary manner from the stabilized activated mixed cultures, obtained as described above, by selection according to their splitting activity (see Methods in Microbiology, Volume 3a, pages 305-361, Volume 3b, pages 1-329, Volume 4, pages 1-460). The strains DSM 1192, DSM 1193, DSM 1194, DSM 1195, DSM 1196, DSM 1197, DSM 1198 and DSM 1199, for example, were isolated in this way.

The pure cultures thus obtained can be cultivated in customary nutrient media. The product to be degraded can thereby be present in the substrate or can be added to the substrate in low concentrations as an inductor, or in individual cases it can be dispensed with completely.

From the resulting pure cultures, it is possible either to obtain an inoculum for further batches by storage, whilst retaining the vitality, or to separate off the micro-organism composition from the culture broth and to dry it carefully in order to obtain the preparation according to the invention in 5. (above). Drying is thereby carried out as already described for obtaining the preparation according to the invention from stabilised activated mixed cultures.

The pure cultures can also be cultivated batch-wise on a large industrial scale as described above.

In the following text, the present invention will be illustrated using a preparation for degrading insecticidal active compounds, preferably phosphorus-containing active compounds, in particular parathion, as an example:

Mixed cultures for the degradation of phosphorus-containing active compounds, in particular parathion, are known (see Munnecke et al., Applied Microbiology, 1974, 28, page 212-217).

A stabilised activated mixed culture can be obtained therefrom by the process according to the invention. The process is carried out in at least 2 passes under the following conditions:

The temperature range is between 20° and 35° C., preferably between 24° and 30° C. and especially between 25° and 28° C.

The pH range is between 6.5 and 9.0, preferably between 7.5 and 7.9 and especially between 7.5 and 7.6.

The phosphorus-containing active compound to be degraded to fed to the culture as the sole source of carbon and energy at a discontinuous flow rate adjusted to correspond to the growth, in a manner such that the concentration of the active compound does not rise about 10 ppm and that of the splitting product p-nitrophenol does not rise above 30 ppm. By the combination of these measures, the mixed culture is stabilised so that it is possible to work under non-sterile conditions without the degrading activity on the active compound changing.

The mixed cultures thus obtained can be used as an inoculum for new fermentations and can be kept at $-18°$ C. for a long period without loss in vitality. The activity yields obtained by these measures are, for parathion, 10-20 times higher than that of a corresponding culture known from the state of the art. If preparations are isolated by suitable drying, for example lyophilisation, from the mixed cultures thus obtained, their activity, per mg of protein, is 10 times higher than that of preparations described hitherto in the art. Surprisingly, preparations of this type can also be kept for a long period, even at room temperature, without being bonded to a carrier.

Pure cultures which degrade phosphorus-containing active compounds, in particular parathion, can be isolated from such mixed cultures.

Surprisingly, such pure cultures can be cultivated in customary complex nutrient media, for example yeast extract, without an additional phosphorus-containing active compound as the growth substrate and an activator which splits phosphorus-containing active compounds. Their activity causing degradation of phosphorus-containing active compounds is surprisingly retained.

A highly active dusting powder which is suitable for industrial purposes can likewise be obtained from these pure cultures by careful drying, for example lyophilisation of the biomass. In contrast to the enzyme solutions hitherto used, this powder is stable for years, even at room temperature. Stable, completely water-soluble enzyme preparations can be obtained by treating an aqueous suspension of this preparation with organic solvents or detergents. Moist cells, which are treated with organic solvents or detergents, can also be used direct as starting materials for producing the soluble enzyme preparation.

In detail, if a parathion-degrading preparation is to be obtained, the procedure is as follows, starting from the abovementioned known mixed culture (see loc. cit.).

1. A medium containing inorganic nitrogen-containing salts, for example $(NH_4)_2SO_4$, and customary nutrient salts are used for activating the known mixed culture. The concentration of these substances can vary within wide limits. Concentrations in the following ranges are preferred: 0.05–0.2 g/l of $MgSO_4$, 0.01–0.05 g/l of $CaCl_2$, 0.1–1.0 g/l of $(NH_4)_2SO_4$, 0.001–0.01 g/l of iron salts, 0.5–5.0 g/l of $K_2HPO_4$ and 0.1–1.0 g/l of $KH_2PO_4$. The pH value is adjusted to between 6.5 and 9.0 by a buffer solution, especially to 7.5–7.9 with phosphate buffer. It is particularly favourable to keep the pH value constant at pH 7.6 by adding NaOH. Such solutions are inoculated with cells from preserves. The amount of inoculum can vary within wide limits. 0.1–5.0 g, in particular 0.5–1.0 g of dry cell substance per 10 l of culture solution is an optimum amount. These cultures are incubated at 20°–37° C., preferably at 24°–30° C., 25°–28° C. being a particularly preferred temperature range.

In order to grow the mixed culture, the parathion is metered in continuously, using a pump, in a manner such that no nitrophenol (splitting product of parathion), or only traces thereof, can be directed during the fermentation. The amount metered in per hour depends on the growth of the culture and is continously increased according to the increase in concentration of the biomass. For example, initially 0.1 ml of parathion per hour and finally 0.75 ml of parathion per hour are fed to a 10 liter culture, during which the parathion concentration in the fermenter should always remain below 10 ppm. The fermentation period is 5–7 days, preferably 6 days. Cell densities of about 1 g dry weight per liter of culture medium are achieved with a pure parathion consumption of 50 ml.

In the case of fermentation batches with which fermentation can be carried out only at low mixing rates, it is advisable to employ a parathion formulation as the source of carbon, by which means a better distribution speed in the fermenter is achieved. It is possible to employ, for example, formulations with organic solvents and emulsifiers. A suitable formulation is, for example: 3 parts of isopropanol, 1 part of parathion and 0.01 part of alkylaryl polyglycol ether.

The splitting activity, on phosphoric acid esters, of culture broths obtained in this manner is 50–100% higher, with about the same fermentation period and metering of parathion, than in the case of cultures which are grown with pure parathion.

Customary complex media, for example yeast extract, yeast autolysate or meat extract media, are best used for producing an active cell culture from pure cultures. In addition, it is also possible to add other sources of carbon, such as organic acids, amino acids, carboxy acids, for example succinic acid, and also nitrophenol. If pure cultures are used, the fermentation time is shortened considerably in comparison with fermentations using mixed cultures and parathion as an organic source of carbon, the activity yields being the same or substantially increased. However, use of pure cultures for producing cell preparations which split P esters necessitates sterile working conditions.

The end points of the fermentations are given by the rates at which the splitting activity of the culture on phosphoric acid esters increases. The culture is interrupted when no further significant increase in activity can be measured.

In order to produce preparations which split phosphoric acid esters, the micro-organism composition is isolated by centrifugation. It is taken up in, for example, 1/10 to 1/20 of the starting volume of distilled water and homogeneously distributed by stirring. The suspension is again centrifuged, the supernatant liquor is discarded and the sediment is again taken up in , for example, 1/50–1/100 of the starting volume of distilled water. This suspension is frozen and then lyophilised. The resulting dry product is water-insoluble but can be readily suspended. It contains the entire splitting activity for phosphoric acid esters.

A simpler drying method, which, however, is associated with certain losses in activity, is the removal of water from the micro-organism sediment, isolated with distilled $H_2O$, by two extractions with, for example, 10 parts by volume (relative to the packed cell volume) of organic solvents, in particular with acetone or ethanol. The dehydrated micro-organism sediment is then dried at 20°–30° C. in a vacuum drying cabinet under 20 mm Hg.

A suspension of fresh or frozen and thawed micro-organism cells in water or a buffer (for example 0.1 M, pH 6–9) is best used as the starting material for producing a dry but water-soluble enzyme preparation. An appropriate suspension of lyophilised micro-organism cells can, however, also be used. The micro-organism cell suspension is incubated with 1–5% of a surface-active substance, such as, for example, Na deoxycholate or Triton X 100, or with 2–10% by volume of butanol at 25°–27° C. for 0.5 to 8 hours, the batch is then centrifuged and the supernatant liquor is then lyophilised directly (in the case where butanol is the solubilising agent) or after prior dialysis against distilled water (if surface-active substances are used). The resulting test preparations contain about 50% of the initial activity, their specific activity is 2–3 times as high as that of the starting material used and they are soluble in water or buffers to give a clear solution.

The examples which follow are intended to illustrate the present invention without implying any restriction of its general applicability. The tests were effected with the aid of parathion-degrading micro-organisms.

EXAMPLE 1

Test for determining the parathion-degrading activity

A 0.1 M potassium phosphate buffer, pH 8.2, a 10%-strength solution of aryloxy polyglycol ether in water and a 1% strength solution of parathion in ethanol are required. To prepare the substrate solution, 0.3 ml of the aqueous emulsifier solution is added to 50 ml of the buffer solution, whilst stirring, and 2 ml of the ethanolic parathion solution are then added slowly.

For the test, 2.4 ml of the above substrate solution are introduced into a cell, temperature-controlled at 25° C. The same substrate solution is also used as the blank. After adjusting the temperature, 100 μl of buffer solution are introduced into the blank cell and 100 μl of the enzyme solution, the suspension or the culture broth, the latter after pre-treatment with toluene (see below), to be tested are introduced into the measuring cell and the change in extinction at 410 nm is recorded and converted to μmols of para-nitrophenol formed or parathion split.

1 enzyme unit (U) is defined as the splitting of 1 μmol of parathion per minute or the liberation of 1 μmol of para-nitrophenol per minute under the above test conditions.

In order to test fresh cells in the culture solution or fresh cell suspensions, these must first be decomposed. For this, 0.2% of toluene is added to the sample to be tested and the mixture is incubated at 30° C. for 30 minutes, whilst shaking. 10 to 100 μl of the sample pre-treated in this manner are tested. In the case of lyophilised or frozen and re-thawed cells, the toluene treatment is superfluous and produces no change in activity of the sample to be tested.

In the examples which follow, the activity in U, as determined above, is given.

EXAMPLE 2

Production of an activated, stabilised mixed culture from the mixed culture, known from the state of the art, which splits P esters To produce an activated, stabilised mixed culture, the following stock solutions were first made up:

Stock solution 1: 1 M K phosphate buffer, pH 7.6
Stock solution 2: 10.0 g of ammonium sulphate, 0.6 g of calcium chloride, 4.0 g of magnesium sulphate and 1,000 ml of water
Stock solution 3: 3.0 g of iron(II) sulphate and 1,000 ml of water
Stock solution 4: customary solution of trace elements.

A mineral salt medium which contains, in 10 liters of water, 100 ml of stock solution 1, 200 ml of stock solution 2 and 10 ml of stock solutions 3 and 4 was used for growing the culture.

The parathion-splitting mixed culture described by Munnecke et al in Applied Microbiology 1974, 28, page 212-217 was used as the starting culture.

The culture was grown in a 10 liter fermenter with 9 liters of the mineral medium. It was inoculated with 1 g of biomass (relative to the dry weight) of the active mixed culture which had been grown as described by Munnecke et al. The fermenter culture was aerated with 10 liters of air per minute at 25°-28° C., whilst stirring (1,200 revolutions/min.). The pH value was adjusted to between 7.5 and 7.6 with 2.5 N NaOH using a titrator. Parathion was used as the growth substrate; it was continuously added to the fermentaton batch in a manner such that the parathion concentration in the fermenter was growth-limiting. This condition prevailed when the actual parathion concentration was below 10 ppm and no nitrophenol could be detected. The cultivation was carried out in 4 successive passes, 1 liter of the preceding growing process being used as the inoculum for the subsequent growing process. The culture period was 3 to 6 days. The cultivation was ended and the next pass was started when only small increases in activity, or no increases in activity, could still be measured in the fermenter batch.

The increase in activity of the mixed culture over the 4 passes is shown in Table 1.

TABLE 1

| Pass No. | Culture period (days) | Activity at the end of fermentation (U/liter) |
|---|---|---|
| 1 | 3 | 31.5 |
| 2 | 3 | 240 |
| 3 | 5 | 820 |
| 4 | 6 | 1,140 |

The activity could not be further increased by growing the mixed culture in a fifth pass. This can be seen from Table 2, in which, in addition to the increase in activity, the metering of the parathion, the amount of parathion consumed during the fermentation and the increase in the biomass are shown, as a function of the fermentation time. The fermentation period was 123 hours. At a total consumption of parathion of 4.4 ml per liter, cell densities of 480 mg of dry weight per liter of culture medium, with a parathion-splitting activity of 1,340 U/liter of culture medium, were achieved; this corresponds to an activity of 2,800 U per g of dry cells.

TABLE 2

Parathion fermentation as a function of time

| Fermentation period (hours) | Activity (U/liter) | Dry weight (g/liter) | Continuous metering (ml/hour) | Parathion consumption (ml) |
|---|---|---|---|---|
| 0 | 119 | 0.045 | | |
| 25 | | | 0.15 | 3.80 |
| 56.5 | | | 0.20 | 10.00 |
| 71.5 | 375 | 0.29 | 0.375 | 15.90 |
| 95.5 | 820 | | 0.500 | 27.90 |
| 119.5 | 1,340 | 0.48 | 0.500 | 39.90 |
| 123 | collected | | 0.750 | 42.50 |

The activated, stabilised mixed culture thus obtained was concentrated to 1/10 of the starting volume by centrifugation and preserved at −18° C. It was used as the starting culture for the further fermentation batches.

EXAMPLE 3

Production of active cell material using a parathion formulation

The culture conditions largely corresponded to those described under Example 2. Instead of pure parathion, a parathion formulation of the following composition was used: 150 ml of isopropanol, 50 ml of parathion and 0.5 ml of alkylaryl polyglycol ether.

8.5 liters of culture medium were inoculated with 80 ml of the preserved mixed culture described in Example 2 and cultivation was carried out for 123 hours. The parathion formulation was metered in continuously. The fermentation was carried out under non-sterile conditions.

The activities of the culture broth obtained at the times indicated, the consumption of parathion and other fermentation data can be seen from Table 3.

TABLE 3

| Fermentation period (hours) | Activity (U/liter) | Dry weight (g of cells/ liter) | Continuous metering (ml/hour) | Formulation consumption (ml) | Parathion consumption (ml) |
|---|---|---|---|---|---|
| 0 | 116 | 0.147 | | 0 | 0 |
| 25 | | | 0.7 | 20 | 5 |
| 56.5 | | | 0.95 | 50 | 12.5 |
| 71.5 | 765 | 0.906 | 1.3 | 75 | 17 |
| 95.5 | 1,030 | | 1.5 | 110 | 27 |
| 119.5 | 2,500 | 1.085 | 1.8 | 150 | 38 |
| 123 | collected | | 2.1 | 165 | 41 |

At a total consumption of pure parathion of 4.2 ml per liter of culture medium, a specific activity of 2,300 U per gram of dry cells was achieved with the parathion formulation.

EXAMPLE 4

Production of the activated mixed culture on a 2,000 liter scale using pure parathion as the substrate 1,000 g of $(NH_4)_2SO_4$, 30 g of $CaCl_2$, 200 g of $MgSO_4$, 3,100 g of $K_2HPO_4$, 600 g of $KH_2PO_4$, 6 g of $FeCl_2$ and 2,000 ml of a solution of trace elements were added to 2,000 liters of de-ionised water.

The 2,000 liter fermentation batch was inoculated with 200 liters of a pre-culture which has been obtained starting from the preserved culture described in Example 2 in passes over 1 liter, 20 liters and 200 liters under the cultivation conditions described in Example 2. The fermentation batch was stirred at 240 revolutions per minute for 138 hours and then at 350 revolutions per minute until the fermentation had ended, and was aerated with 2,000 liters of air per minute. The temperature was 27°-28° C. The pH value was kept constant at 7.5–7.7 with 2.5 N NaOH. The parathion was added continuously at the rates of metering indicated in the table. The course of the fermentation can likewise be seen from Table 4.

TABLE 4

Parathion fermentation on a 2,000 liter scale with respect to time

| Fermentation period (hours) | Activity (U/liter) | Dry weight (G/liter) | Continuous parathion metering (ml/hour) | Parathion consumption (ml) |
|---|---|---|---|---|
| 0 | 75 | | | 0 |
| 8 | | | 20 | 160 |
| 72 | 103 | 0.17 | 30 | 2,080 |
| 120 | 334 | | 40 | 4,000 |
| 148 | 384 | | 60 | 5,680 |
| 168 | 500 | 0.537 | 100 | 7,680 |

At a parathion consumption of 3.8 ml per liter of culture medium, a specific activity of 940 U/g of dry cells was achieved.

EXAMPLE 5

Production of active cell material using an isopropanol formulation at a slow rate of mixing in the fermenter (200 revolutions per minute)

5 liters of nutrient solution were inoculated with 10 ml of concentrated activated mixed culture from Example 2, which had been stored at −18° C. for 7 days, in a 7 liter fermenter and the batch was stirred at 200 revolutions/minute and aerated with 6 liters of air/minute. The cultivation temperature was 27° C.; the pH value was 7.6 0.5 ml of a formulation of parathion in isopropanol (composition: see Example 3) was first added discontinuously and the batch was incubated for 15 hours. Thereafter, the parathion formulation was added continuously at the metering rate indicated in Table 5. The increase in the activity and the dry weight of the biomass can likewise be seen from Table 5.

TABLE 5

Parathion fermentation at a low rate of mixing, with respect to time

| Fermentation period (hours) | Activity (U/liter) | Dry weight (g/liter) | Continuous parathion formulation metering (ml/hour) | consumption (ml) | Parathion consumption (ml) |
|---|---|---|---|---|---|
| 15.0 | | | | 0.5 | 0.1 |
| 30.5 | 343 | | 0.7 | 21.0 | 5.2 |
| 48.0 | 580 | 0.45 | 1.15 | 41.1 | 10.3 |
| 57.5 | | | 1.3 | 54.0 | 13.5 |
| 72.0 | 860 | 0.98 | 1.5 | 75.8 | 19.0 |

At a consumption of pure parathion of 3.8 ml per liter of culture medium, a specific activity of 880 U/g of dry cells was achieved.

EXAMPLE 6

Production of active cell material from pure cultures 9 liters of a complex medium having the composition: 1 g of $NaHCO_3$, 8 g of yeast autolysate, 3 g of meat hydrolysate (Danimex) and 1,000 ml of $H_2O$, were inoculated with 500 ml of a pre-culture, grown in a complex medium for 3 days, of the Pseudomonas isolate Pseudomonas spec. (DSM Göttingen, No. 1193), which splits P esters, and the batch was stirred at 1000 revolutions per minute at 28° C. and aerated at 9 liters/minute. The pH value was 7.6. The fermentation period was 21 hours. After this time, the parathion-splitting activity of the fermentation batch was 5,200 U/liter of culture medium. The specific activity of the cells was 1,620 U/g of dry weight.

EXAMPLE 7

The Pseudomonas strains deposited in the Deutschen Sammlung Mikroorganismen (German Collection of Microorganisms) under Numbers 1193, 1195, 1196, 1197 and 1194 were grown as shake cultures in nutrient broth (Difco) and, after the highest activity was reached, the parathion hydrolase activity was measured.

The hydrolase activities in U/mg of cell protein[1] are summarised in Table 6.

TABLE 6

| Strain No. (DSM) | Specific activity, U/mg of protein (1) |
|---|---|
| 1193 | 0.12 |
| 1195 | 0.83 |
| 1196 | 1.21 |

TABLE 6-continued

| Strain No. (DSM) | Specific activity, U/mg of protein (1) |
| --- | --- |
| 1197 | 2.04 |
| 1194 | 0.2 |

(1) The cells were decomposed with ultra-sound; the test after the ultra-sound treatment was carried out as described under Example 1.

EXAMPLE 8

The Pseudomonas strains deposited in the Deutschen Sammlung Mikroorganismen (German Collection of Microorganisms) under Nos. DSM 1192, DSM 1198 and DSM 1199 were incubated in the complex medium described under Example 6 at 30° C. for 2 days, with shaking. The parathion-splitting activities of the strains per liter of culture medium are summarised in Table 7.

TABLE 7

| Strain No. (DSM) | Activity, U/liter |
| --- | --- |
| 1192 | 1,240 |
| 1198 | 785 |
| 1199 | 520 |

EXAMPLE 9

5 liters of an activated mixed culture with an activity of 890 U/liter, which had been cultivated as described in Example 2, were centrifuged at 4,000 revolutions per minute in a cooled centrifuge from Messrs. Hettich at 4° C. for 30 minutes. The inactive supernatant liquor was poured off, 500 ml of distilled $H_2O$ were added to the sediment and the mixture was stirred with a magnetic stirrer for 10 minutes. The homogeneous cell suspension (550 ml, 7,100 U/liter) was again centrifuged as above, the inactive supernatant liquor was discarded and this time 100 ml of distilled $H_2O$ were added to the sediment and the mixture was stirred as above. The resulting 130 ml of cell suspension (27,300 U/liter) were frozen at −18° C. and then freeze-dried. Yield: 3.3 g of a preparation with an activity of 750 U/g.

EXAMPLE 10

The cell slurry of 4,000 liters of a culture broth, which had been produced in 2 batches according to Example 4, was concentrated (200–300 liters) in a separator from Messrs. Westfalia and the inactive clear runnings were discarded. The cell mass was sedimented from the slurry in a basket centrifuge at 2,500 revolutions per minute. The sediment was taken up in 300 liters of distilled water and suspended by stirring. It was again sedimented in the basket centrifuge, the washed cell sediment was taken up in 30–40 liters of distilled water and suspended and the suspension was frozen at −40° C. and then lyophilised. Yield: 981 g with an activity of 700 U/g.

EXAMPLE 11

100 ml of a cell suspension which had been produced as described in Example 2 and had been washed, then frozen and stored at −18° C. for 1 month, was thawed and centrifuged at 10,000 revolutions per minute (4°) for 20 minutes. The supernatant liquor (200 U/liter) was discarded. The cell sediment was re-suspended in 100 ml of water and the suspension was divided (6,830 U/liter). One half was lyophilised direct. Yield: 1.25 g with an activity of 175 U/g.

The other half was again centrifuged at 10,000 revolutions per minute and the bacteria sediment was extracted at 4° C. with 2×50 ml of analytical grade acetone. The acetone extracts were discarded and the residue was dried at room temperature in a vacuum drying cabinet. Yield: 0.9 g with an activity of 150 U/g.

EXAMPLE 12

12 liters of a culture broth, produced according to Example 2, with an activity of 125 U/liter were centrifuged at 4,000 revolutions per minute for 30 minutes, the supernatant liquor was discarded and the sediment was taken up and suspended in 500 ml of water (3,000 U/liter). It was again centrifuged off, the supernatant liquor was discarded and the sediment was re-suspended in water to make up to 120 ml. This solution was used as the starting solution for the solubilising experiments in Example 6 and 7.

EXAMPLE 13

30 ml of 0.1 M K phosphate buffer, pH 8.2, were added to 30 ml of the suspension from Example 4 (test suspension 4,800 U/liter, 10,000 g supernatant liquor: U/liter=0). 3 g of sodium deoxycholate were now added and the batch was incubated at 30° C. for 30 minutes in a shaking waterbath. The batch was then centrifuged under 10.000 g for 30 minutes at 40° C. The supernatant liquor now had an activity of 19,930 U/liter. The supernatant liquor was introduced into a dialysis tube and was dialysed against distilled water at 4° C. The originally viscous solution thereby became clear; the retained material was centrifuged at 19,000 revolutions per minute and the clear supernatant liquor was lyophilised. Yield: 1.4 g of water-soluble enzyme with an activity of 320 U/g.

EXAMPLE 14

30 ml of 0.1 M K phosphate buffer, pH 8.2, were added to 30 ml of the suspension from Example 4 (test suspension 4,800 U/liter, 10,000 g supernatant liquor U/liter=0). 6 ml of n-butanol were then added and the batch was shaken at 30° C. for 30 minutes in a shaking waterbath. The batch was centrifuged under 10,000 g for 30 minutes. The supernatant liquor now had an activity of 13,700 U/liter.

25 ml of the supernatant liquor were directly lyophilised. Yield: 300 mg of a water-soluble preparation with an activity of 890 U/g.

25 ml of the supernatant liquor were first dialysed against distilled water and then lyophilised. Yield: 120 mg with an activity of 1,760 U/g.

EXAMPLE 15

16 liters of a culture broth with an activity of 120 U/liter, obtained as described under Example 2, were centrifuged at 4,000 revolutions per minute, the supernatant liquor was discarded and the sediment was taken up in 500 ml of water and re-suspended. The suspension was again centrifuged and the sediment was taken up in 100 ml of distilled water. 100 ml of 0.1 M glycine/NaOH buffer, pH 8.5, were added to this cell suspension and the batch was homogenised for a short time on an Ultraturax homogeniser (test suspension 956 U/liter, 10,000 g supernatant liquor 550 U/liter). 15 ml (=7.5% by volume) of butanol were now added to the batch and the batch was incubated at 37° C. for 1 hour, whilst stirring. It was subsequently cooled to 4° C. and then centrifuged at 19,000 revolutions per minute for 30 minutes. The supernatant liquor had an activity of 9,150 U/liter. The sediment was taken up in 100 ml of water and the suspension was again centrifuged. This second supernatant liquor (2,860 U/liter) was combined with the first (280 ml, 7,650 U/liter). 190 ml of this solution were directly lyophilised. Yield: 1.4 g of soluble preparation with an activity of 1,090 U/g. 90 ml of the solution were first dialysed against water and then lyophilised.

Yield: 0.5 g of a soluble preparation with an activity of 1,370 U/g.

EXAMPLE 16

6 liters of a fermentation broth from a fermentation batch according to Example 6 were centrifuged at 4,000 revolutions per minute and at 40° C. for 30 minutes. The sediment was re-suspended in 500 ml of water and the suspension was again centrifuged as above. The supernatant liquor was discarded, the sediment washed in this manner was suspended in 100 ml of water and the suspension was frozen and lyophilised.

EXAMPLE 17

Degradation of parathion in containers 30 liters of water were introduced into a 120 liter metal container for storing parathion, which, after emptying, contained 40–60 g of parathion as a residual contaminant; the contents were thoroughly mixed and the pH value was adjusted to 8.3. Degradation of the parathion was initiated with 400 mg of the preparation obtained according to Example 10. At a conversion rate of 90–120 mg per minute, the degradation of the parathion had ended in 10 hours.

EXAMPLE 18

Enzymatic degradation of parathion in wet sand.

200 ml of distilled water and 1 g of analytical grade $NaHCO_3$ were added to 500 g of sand (0.76% loss on drying at 140° C.). 425.5 mg of a 47% strength parathion formulation were added, the components were mixed and 20 mg of the preparation produced according to Example 10 were added. After a mixing time of 2.5 hours, the mixture was rendered alkaline and filtered and the p-nitrophenol in the filtrate was immediately determined photometrically. Content: 490 g of p-nitrophenol/liter, that is to say the degradation was 100% of theory.

We claim:

1. A process for the production of a storage-stable material capable of degrading a waste product comprising at least one of phosphate esters and acrylonitrile, comprising cultivating a mixed culture of microorganisms capable of growing on the waste product by feeding in the waste product at a progressively increasing concentration which does not kill the microorganisms due to by-product formation, terminating the cultivation when the waste product-splitting activity of the culture has leveled off, separating at least a portion of the now active mixed culture and repeating the cultivation at least once to produce a stabilized active mixed culture, treating the stabilized active mixed culture chemically, and then drying to obtain a storage-stable active mixed culture.

2. A process according to claim 1, wherein the microorganisms are protozoa, algae, blue-green algae, yeasts, fungi, bacteria and mixtures of any of these.

3. A process according to claim 1, wherein the culture conditions include a temperature of 10°–70° C., a pH-value of 1–10, a phosphate ($PO_4^{3-}$) content of 0.08–10 g/liter, a nitrogen salt content (as $NH_4Cl$) of 0–50 g/liter, a magnesium content (as $MgSO_4$) of 0.01–2 g/liter, an iron salt content of 0.04–0.1 g/liter, a calcium content (as $CaCl_2$) of 0.00–0.1 g/liter, an oxygen concentration of 0–48 mg/liter, and a culture period of between 1 hour and 14 days.

4. A process according to claim 1, wherein an emulsifying agent and/or a dispersing agent are present in the culture medium.

5. A process according to claim 1, wherein the conversion is effected in from 2 to 50 passes.

6. A process according to claim 1, wherein the stabilized activated mixed culture is rendered storage-stable by freezing, by lyophilisation, by the removal of water with an organic solvent, by spray-drying or by the addition of a preserving chemical.

7. A process according to claim 1, wherein the mixed culture comprises a mixture of protozoa, algae, blue-green algae, yeast, fungi or bacteria with one another or with each other.

8. A process according to claim 1, wherein the initial mixed culture is a storage-stable active mixed culture from a prior cycle.

9. The product produced by the process of claim 1.

10. A process according to claim 1, wherein the culture medium is a yeast extract, yeast autolysate or meat extract medium with or without an additional other source of carbon and/or nitrogen and as organic acids, amino acids, carbohydrates or nitrophenol.

11. A process according to claim 1, wherein the waste product comprises a phosphate ester.

12. A process according to claim 1, wherein the waste product comprises acrylonitrile.

13. A biologically pure culture of Pseudomonas strain DSM 1192 or 1193, said culture being capable of forming a stabilized mixed culture capable of degrading products of industrial organic syntheses.

* * * * *